(12) United States Patent
Kristen

(10) Patent No.: US 12,357,790 B2
(45) Date of Patent: Jul. 15, 2025

(54) CANNULA UNIT

(71) Applicant: Roche Diabetes Care, Inc., Indianapolis, IN (US)

(72) Inventor: Thomas Kristen, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/264,930

(22) Filed: Feb. 1, 2019

(65) Prior Publication Data

US 2019/0160258 A1  May 30, 2019

Related U.S. Application Data

(63) Continuation of application No. PCT/EP2017/070902, filed on Aug. 18, 2017.

(30) Foreign Application Priority Data

Aug. 19, 2016 (EP) ..................................... 16185040

(51) Int. Cl.
*A61M 25/00* (2006.01)
*A61M 5/142* (2006.01)
(Continued)

(52) U.S. Cl.
CPC .... *A61M 25/0097* (2013.01); *A61M 5/14244* (2013.01); *A61M 25/0014* (2013.01);
(Continued)

(58) Field of Classification Search
CPC .............. A61M 39/12; A61M 39/0247; A61M 5/14244; A61M 25/0014; A61M 39/04; A61M 2207/10; A61M 25/0097; A61M 2039/027; A61M 39/02; A61M 2039/0261; A61M 2039/0282; A61M 2039/0276; A61M 2039/0279; A61M 2039/0294; A61M 39/10; A61M 2039/0205;
(Continued)

(56) References Cited

U.S. PATENT DOCUMENTS 4,430,081 A    2/1984  Timmermans
4,781,703 A *  11/1988 Walker .............. A61M 25/0014
                                                604/264
(Continued)

FOREIGN PATENT DOCUMENTS

| JP | WO 2007/0056504 A1 | 5/2007 |
| WO | WO 99/21605 A2 | 5/1999 |
| WO | WO 02/07804 A1 | 1/2002 |
| WO | WO 2011/089193 A2 | 7/2011 |

OTHER PUBLICATIONS

International Search Report and Written Opinion, PCT/2017/070902, Oct. 17, 2017, 12 pages.

*Primary Examiner* — Kevin C Sirmons
*Assistant Examiner* — Avery Smale
(74) *Attorney, Agent, or Firm* — Bose McKinney & Evans LLP

(57) ABSTRACT

A cannula unit comprises a housing and a flexible cannula. The flexible cannula is provided with an end area that deviates from the shape of the rest of the flexible cannula. Said end area of the flexible cannula has, e.g., a funnel-like shape or the shape of a flange. The end area of the flexible cannula is positively locked to the housing by clamping.

26 Claims, 4 Drawing Sheets

(51) Int. Cl.
  *A61M 5/158*  (2006.01)
  *A61M 39/02*  (2006.01)
  *A61M 39/04*  (2006.01)
  *A61M 39/12*  (2006.01)
(52) U.S. Cl.
  CPC ........ *A61M 39/0247* (2013.01); *A61M 39/04* (2013.01); *A61M 39/12* (2013.01); *A61M 5/158* (2013.01); *A61M 2039/027* (2013.01); *A61M 2207/00* (2013.01); *A61M 2207/10* (2013.01)
(58) Field of Classification Search
  CPC .. A61M 2039/0273; A61M 2039/0291; A61M 5/14248; A61M 2005/14272; A61M 5/14276; A61M 5/14; A61M 5/142; A61M 25/0009; A61M 25/0021; A61M 25/0023; A61M 25/0041; A61M 25/0043; A61M 2039/0036; A61M 2039/0063; A61M 2039/0072; A61M 39/08; A61M 2039/087; A61M 2205/0216
  See application file for complete search history.

(56) References Cited

U.S. PATENT DOCUMENTS

| | | | |
|---|---|---|---|
| 5,304,156 A | 4/1994 | Sylvanowicz et al. | |
| 2005/0101932 A1* | 5/2005 | Cote | A61M 5/158 604/506 |
| 2006/0264904 A1* | 11/2006 | Kerby | A61M 25/0021 604/523 |
| 2007/0005001 A1* | 1/2007 | Rowe | A61M 25/0014 604/19 |
| 2008/0243085 A1* | 10/2008 | DeStefano | A61M 5/158 604/180 |
| 2008/0288144 A1 | 11/2008 | Jeppe et al. | |
| 2012/0296290 A1 | 11/2012 | Argauer et al. | |
| 2013/0184541 A1* | 7/2013 | Antonio | A61B 5/0002 604/533 |
| 2014/0039453 A1* | 2/2014 | Sonderegger | A61M 5/158 604/506 |
| 2014/0350485 A1* | 11/2014 | Sonderegger | B29C 45/1657 604/533 |

* cited by examiner

CANNULA UNIT

RELATED APPLICATIONS

This application is a continuation of PCT/EP2017/070902, filed on Aug. 18, 2017, which claims priority to EP 16 185 040.9, filed on Aug. 19, 2016, the entire disclosures of both of which are hereby incorporated herein by reference.

BACKGROUND

This disclosure relates to cannula units for infusion site interfaces and infusion pumps, as well as manufacturing methods for such cannula units.

Infusion pumps are used for parenterally providing patients with liquid medicaments over longer time periods. Nowadays, infusion pumps with very small dimensions are available that can be carried by the patient on the body. Such small-sized ambulatory infusion pumps are particularly useful for metering small doses of highly effective liquid medicaments, such as insulin for the treatment of diabetes, or analgesics for pain therapy, which are conveyed through a cannula into the tissue of a patient.

In one approach, an infusion pump, carried somewhere on the body, e.g., attached to a belt, is fluidly connected via flexible tubing to an infusion site interface, also called insertion head, that is attached to the body of the patient. The infusion site interface comprises a cannula unit with a cannula to be inserted into the body tissue, a housing to which the cannula is mounted, and connector means for fluidly connecting the cannula with the flexible tubing connected to the upstream infusion pump. The tubing can be repeatedly connected and disconnected from the infusion site interface. The connector means may for example comprise a septum sealingly closing the fluid system of cannula and housing. The septum can be penetrated by a hollow needle, for reversibly establishing a fluid connection. The cannula is preferably made of a flexible material. Such cannulas are more comfortable for their users, particularly during body movements. Since flexible cannulas cannot be inserted directly into the tissue, an additional piercing device, e.g., in the form of a rigid piercing needle made from metal, is arranged inside the flexible cannula. A pointed end of the piercing device protrudes from the proximal end of the cannula, the cannula that will be open toward the interstitial fluid. After inserting the piercing device and the stabilized cannula into the body tissue, the piercing device is removed from the cannula. The cannula is now flexible, and remains in the body tissue. Generally, a piercing needle is arranged in such a way that it penetrates a septum, which after withdrawal of the piercing needle sealingly closes the distal end of the now open cannula fluid path. Examples of such infusion site interfaces and insertion heads are shown in WO 02/07804 A1, US 2008/0288144 A1, and US 2012/296290 A1, the disclosure of which is hereby included by reference in their entirety.

In another approach, the infusion pump device is directly fluidly connected with the infusion site interface. Examples of such embodiments are shown in WO 2007/056504 A1, the disclosure of which is hereby included by reference in its entirety. The fluid connection between pump and cannula is established by a hollow connector needle of the pump, reversibly penetrating a septum of the cannula unit that sealingly closes the distal end of the cannula fluid path. Advantageously, the pump can be repeatedly connected and disconnected from the infusion site interface.

In a common method for manufacturing infusion site interfaces with flexible cannulas, in a first step a stabilizing pin is introduced into the flexible cannula, for simplifying the handling of the flexible cannula during the manufacturing process. The temporary structural unit prepared in this manner is inserted into a previously manufactured housing, the flexible cannula and the housing are permanently connected, for example by a thermal process. The stabilizing pin is then drawn out of the flexible cannula, and is replaced by the actual piercing device. The insertion of the piercing devices sometimes damages the flexible cannulas, which results in comparably high rejection rates during manufacturing.

In the known manufacturing methods for cannula units, a considerable number of elaborate manufacturing steps are involved, for example injection molding in very small dimensions and with very small dimensional tolerances. Due to the accumulation of possible deviations from nominal values during the manufacturing steps of the various elements, as well as during the assembly steps, there is a considerably high rejection rate, in order to avoid any risk of malfunction of the manufactured devices, e.g., leakage.

In order to simplify the manufacturing process and to reduce the rejection rates during manufacturing, U.S. Publication No. 2012/0296290 A1 discloses an advantageous manufacturing method for cannula units. A flexible cannula is threaded onto a piercing needle instead of a temporary stabilizing pin. In one embodiment, the distal end of the cannula has a diameter that increases towards the end, compared to the constant diameter of the rest of the cannula. The housing is injection moulded around the distal end of the cannula, and the directly adjacent piercing pin. As a result, the cannula is form-locked inside the housing body. When the piercing needle is drawn out of the cannula, a channel is formed in the housing body that continues the cannula fluid channel toward a fluid chamber of the housing. While such a cannula unit has many advantages, the necessary injection molding process is demanding and requires special tooling. Furthermore, the flexible cannula will be compressed to a certain extent during manufacture, due to the high pressures involved in the injection molding step, and essentially remains in this state after manufacture. The compressed cannula wall exerts a force directed radially inwards onto the insertion needle, which may lead to a considerable while undefined increase of the friction force between the flexible cannula and the insertion needle. This may cause crumpling or even rupture of the flexible cannula during the withdrawal of the insertion needle. At the same time the friction force between flexible cannula and insertion needle should not be too low, in order to avoid problems such as crumpling during insertion of the cannula into the subcutaneous tissue of the patient, which may also be a source for malfunctions and leaks. The involved forces and the influence of the production parameters on the resulting forces are difficult to predict and to control.

There is thus an ongoing need for improvement in the field of cannula units for infusion site interfaces and infusion pumps, and corresponding manufacturing methods.

SUMMARY

This disclosure teaches cannula units for ambulatory infusion pumps, and manufacturing method for such cannula units, which overcome one or more of the above-mentioned problems and other problems, and particularly reduce potential malfunctions due to accumulated deviations from nominal production parameters.

This disclosure also provides a manufacturing method with reduced manufacturing costs, particularly decreased expenditures for tooling and facilities.

This disclosure also teaches an increase in the reliability of a manufacturing process for cannula units, and to provide cannula units that are reliable and cost efficient in large scale manufacture.

A first aspect of this disclosure concerns an advantageous method for manufacturing a cannula unit. Such a method for manufacturing a cannula unit according to this disclosure comprises the steps of: providing a flexible cannula with an end area that deviates from the shape of the rest of the cannula; providing a housing; and connecting the end area of the flexible cannula to the housing; wherein the end area of the flexible cannula is positively locked to the housing by clamping.

In the context of the present disclosure, 'clamping' of an object is to be understood in the common technical sense of firmly fastening said object between two or more further objects by friction-lock, or by friction lock in combination with form-lock. The clamped first object is subject to a certain force, in order to achieve the friction lock, which is achieved by moving the further objects into a certain position in regard to the first object, and permanently holding the further objects in that position.

Clamping the cannula to the housing considerably simplifies the assembly process, since, e.g., no complex injection molding tooling is needed for connecting the cannula and the housing.

Furthermore, clamping a flexible cannula to the housing, which consists of a compressible or even elastic material, achieves a sealing connection with the housing, which would not be possible if the cannula would be made of a rigid material such a steel.

Advantageously, the end area of the flexible cannula is connected to the housing by crimping.

In the context of the present disclosure, 'crimping of an object to another object is to be understood in the common technical sense of firmly fastening said object to the other object, by deforming one or both of the objects, in order to achieve a friction lock and form-lock. Thus crimping can be understood as a special form of clamping.

Alternatively, or in addition, the end area of the flexible cannula is connected to the housing by clamping the end area of the flexible cannula between a first part and a second part of the housing.

In such a variant of the method according to this disclosure, the first part and the second part of the housing are advantageously provided as two separate parts. Even more advantageously, after clamping the end area of the flexible cannula to the housing, the first part and the second part of the housing are permanently connected, e.g., by ultrasonic welding and/or adhesive bonding.

Alternatively, the housing is realized as one monolithic element.

In the above-mentioned variants of methods according to this disclosure, advantageously a piercing element, e.g., a piercing needle, is mounted to the cannula unit, by threading the piercing element or needle on the cannula.

Furthermore, advantageously a septum is mounted to the housing, e.g., by crimping.

A second aspect of this disclosure concerns an advantageous cannula unit. Such a cannula unit according to this disclosure comprises a housing, and a cannula provided with an end area deviating from the shape of the rest of the cannula. Said end area of the flexible cannula has e.g., a funnel-like shape, or the shape of a flange. The end area of the flexible cannula is positively locked to the housing by clamping.

Advantageously, the end area of the flexible cannula is crimped to the housing.

Alternatively, or in addition, the end area of the flexible cannula is clamped between a first part and a second part of the housing. Even more advantageously, the first part and the second part of the housing are separate parts.

In an advantageous cannula unit as described above, the first part and the second part of the housing advantageously are permanently connected to each other, e.g., by ultrasonic welding and/or by adhesive bonding.

Alternatively, the housing of a cannula unit according to this disclosure is realized as one monolithic element.

In the above-mentioned embodiments of cannula units according to this disclosure, advantageously a piercing element, e.g., a piercing needle, is threaded on the cannula.

In further advantageous embodiments of such cannula units according to this disclosure, a septum mounted to the housing, e.g., by crimping.

Cannula units according to this disclosure can be manufactured using manufacturing methods according to this disclosure.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

In order to facilitate a fuller understanding of this disclosure, reference is now made to the appended drawings. These references should not be construed as limiting this disclosure, but are intended to be exemplary only.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Components that are identical, or that are identical at least in terms of their function, are designated below by identical or at least comparable reference numbers.

Figure 1:
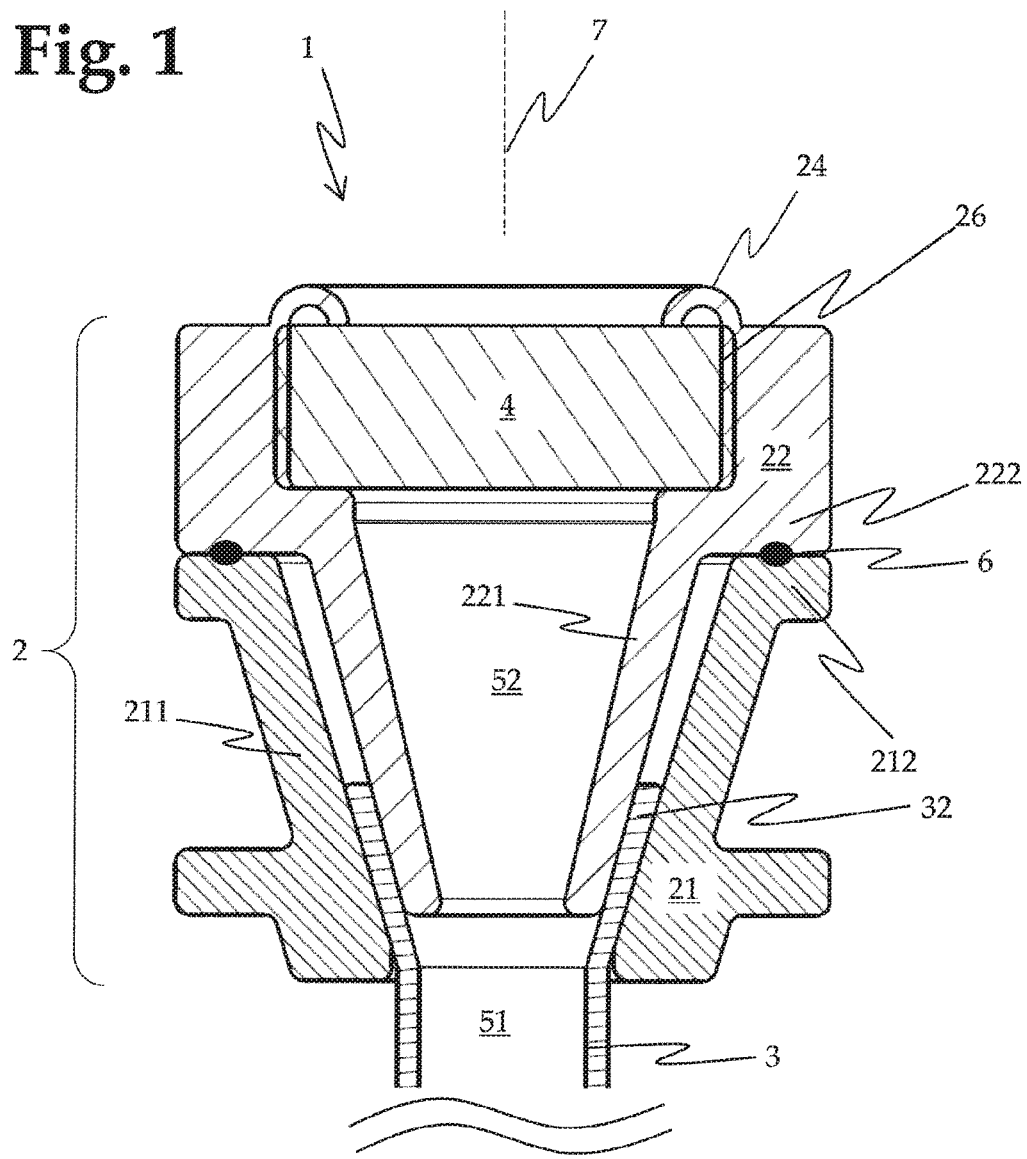
FIG. 1 schematically shows a cross section of a first embodiment of a cannula unit according to this disclosure.

A first embodiment of a cannula unit 1 according to this disclosure is disclosed in a cross-sectional view in FIG. 1. The assembled cannula unit 1 comprises a flexible cannula 3, of which the distal end, the end opposite to the body of the patient, is visible, and a housing body or housing 2, to which the cannula 3 is mounted. The outer shape of housing body 2 is chosen such that the housing body, and thus the cannula unit 1, can be mounted, e.g., to an infusion site interface.

The body of the housing comprises a first part 21, having a receptacle 211 in the form of a conical through-hole along the longitudinal axis 7, and a second part 22, having a cone-shaped bushing 221 with a through-hole along longitudinal axis 7. The two parts 21, 22 of housing body 2 are advantageously made from a suitable polymer material for medical appliances, advantageously a thermoplastic polymer, such as, e.g., methyl methacrylate acrylonitrile-butadiene-styrene (MABS), polycarbonate (PC), polymethylmethacrylate (PMMA), polypropylene (PP), polyethylene (PE) and the like, and are advantageously produced by injection molding. Advantageously, both parts should be manufactured from the same material. The flexible cannula is also advantageously made from a suitable polymer material such as polytetrafluoroethylene (PTFE), linear low-density polyethylene (LLDPE), low density polyethylene (LDPE), high density polyethylene (HDPE), or the like.

The housing body, namely in the given embodiment its second part 22, comprises an inner chamber 52 formed by the through-hole, opening on a proximal end, the end facing the body of a patient, toward the fluid channel 51 of cannula 3. An upper, distal end of the fluid chamber 52 is sealingly closed by an essentially cylindrical elastomeric septum 4 arranged in a corresponding seat 26 of second part 22, and is held in place by a crimp connection 24. The dimensions of circular septum 4 and the corresponding circular seat 26 of body 2 are chosen such that the septum is radially compressed, thereby achieving a fluid-tight seal between second body 2/second part 22 and septum 4.

The opening at the distal end of cannula 3 has a diameter that is larger than the diameter of the rest of the cannula, and has a funnel-like shape 32. The funnel-like cannula end 32 is clamped between the conical bore 211 of first part 21 and the conical bushing 221 of second part 22. The first 21 part and the second part 22 are advantageously permanently connected. In the shown embodiment, the two parts 21, 22 of the housing body 2 are bonded at two abutting flanges 212, 222 of the two parts 21, 22 by ultrasonic welding 6. Other suitable methods for connecting two such parts are known to the skilled person, e.g., adhesive bonding.

The geometry and dimensions of the bore 211 of first part 21, the bushing 221 of second part 22, and the funnel-shaped distal end 32 of the flexible cannula 3 are chosen such that when the two flanges 212, 222 abut each other, the funnel-shaped cannula end 32 is positively locked between the bore 211 and the bushing 221. Advantageously, the thickness of the wall of the cannula 3, particularly of its funnel end 32, is chosen such that the cannula wall is compressed to a certain extent between bore 211 and bushing 221, thereby achieving a fluid-tight sealing connection between flexible cannula 3 and second part 22 of body 2, and thus between the fluid channel 51 of cannula 3 and the fluid chamber 52 of body 2. In addition, such a connection provides increased resistance against slipping off of flexible cannula 3 from body 2, due to the increased friction.

The inclination of the surfaces of cones 211 and 221 that face each other can be chosen identical. Alternatively, the inclination in regard to longitudinal axis 7 of the outer surface of conus 221 can be chosen a few degrees larger than the inclination of the inner surface of conus 211. As a result, the distance between the two conus surfaces is smallest at the proximal edge of conical bushing 221, and the cannula end is clamped in a circular area at the end of bushing 221. This allows to increase the achievable clamping force.

In another alternative, one or more circumferential rips or similar protruding structural elements can be provided on conical bushing 221 and/or conical bore 211, in order to increase friction between cannula funnel surface and cone surface.

A cannula unit according to the first embodiment as discussed above allows to realize an assembly process that comprises less steps, and involves less possible sources for leakage and other malfunctions.

In a first step, an end of a flexible cannula 3 is provided with an opening with increased diameter. For example, the opening of an endless cannula can be expanded by suitable conical tooling. Form and size of the opening are chosen such that the end of a conical bushing 221 can be placed in the expanded opening of cannula 3. After inserting the conical bushing in the expanded opening of cannula 3, the cannula end is thermally shrunk onto the conical bushing 221, resulting in a funnel-shaped distal cannula end 32. The mechanical connection between second part 22 and cannula 3 has only to be stable enough for the following manufacturing steps.

For the steps above, the cannula may be cut to length before or after expanding the opening, or after mounting the cannula end to the conical bushing. The latter variant has the particular advantage that the trimmed loose cannula does not have to be handled as a separate element, and can be easily handled in the manufacturing process by holding second part 22.

The cannula 3 and the conical bushing 221 of second part 22, to which it is attached, are threaded through the through-hole of first part 21, until the flanges 211, 221 of the two parts of body 2 abut each other. The funnel-shaped cannula end 32, and thus also the conical bushing 221, is automatically precisely aligned to the longitudinal axis 7 by conical bore 211. The two parts 21, 22 are then permanently connected, e.g., by ultrasonic welding. The mounting of cannula 3 on body 2 is completed.

In a subsequent step, the septum 4 is inserted into the provided seat 26 in second part 22, and a crimp connection 24 is established, by thermally treating a corresponding cylindrical wall structure of body 2 and crimping the wall over the distal surface of the septum 4, arriving at the state in FIG. 1.

In case the cannula 3 is a flexible cannula, the cannula unit 1 shown in FIG. 1 is not yet completed. A piercing needle needs to be threaded into the cannula, in order to obtain the temporary rigid piercing needle/cannula structure. For that purpose, a piercing needle is pierced from above through septum 4 and is threaded through the cannula 3, until its end protrudes from the proximal end of cannula 3.

In an alternative approach, the above-mentioned manufacturing method can by modified as follows: The piercing needle is threaded onto the flexible cannula directly after expanding one end of the cannula, or after mounting the cannula end to the conical bushing 221. The following manufacturing steps remain unchanged, expect for the fact that for mounting septum 4 in the corresponding seat of second part 22, the septum is pushed over the piercing means into place in the seat 26, the distal end of the piercing means piercing the septum in this process. Then the crimp connection 24 is completed. This approach has the advantage that the step of threading the piercing means onto the cannula, which has a higher discard rate than other steps, takes place in an early stage, such that the costs involved with discarding damaged intermediate products is minimal. The final cannula unit, however, is identical to a cannula unit where the piercing needle is mounted later, as described further above.

Depending on the application of the cannula unit, the body 2 can now be mounted to an overall structure, e.g., of an infusion site interface. The piercing needle can be provided with a handle that allows a user to withdraw the needle after insertion of the needle/cannula structure into the body tissue, or can be connected to a device that allows the automatic withdrawal of the needle, as for example disclosed in U.S. Publication No. 2008/0228144 A1 as cited further above.

In the embodiment discussed above, the distal end area of the cannula has to have a certain shape, in order to achieve the required technical function. While an end area of a flexible cannula can be shaped without problems with corresponding tooling, such shaping would be difficult to achieve or even impossible with rigid cannulas such as steel cannulas, which furthermore would miss the needed compressibility to achieve a sealing connection between the different parts.

Figure 2:
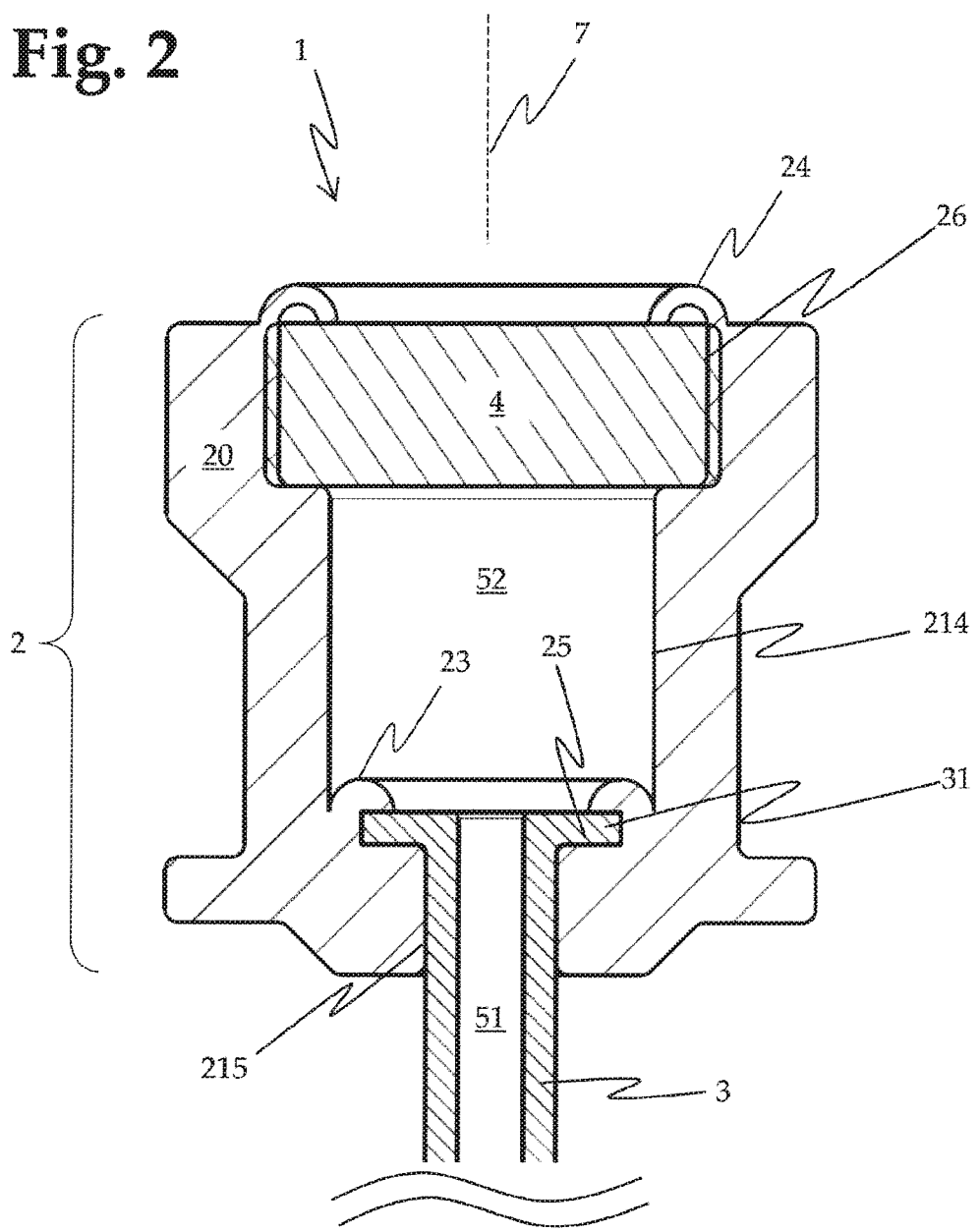
FIG. 2 schematically shows a cross section of a second embodiment of a cannula unit according to this disclosure.
Figure 3:
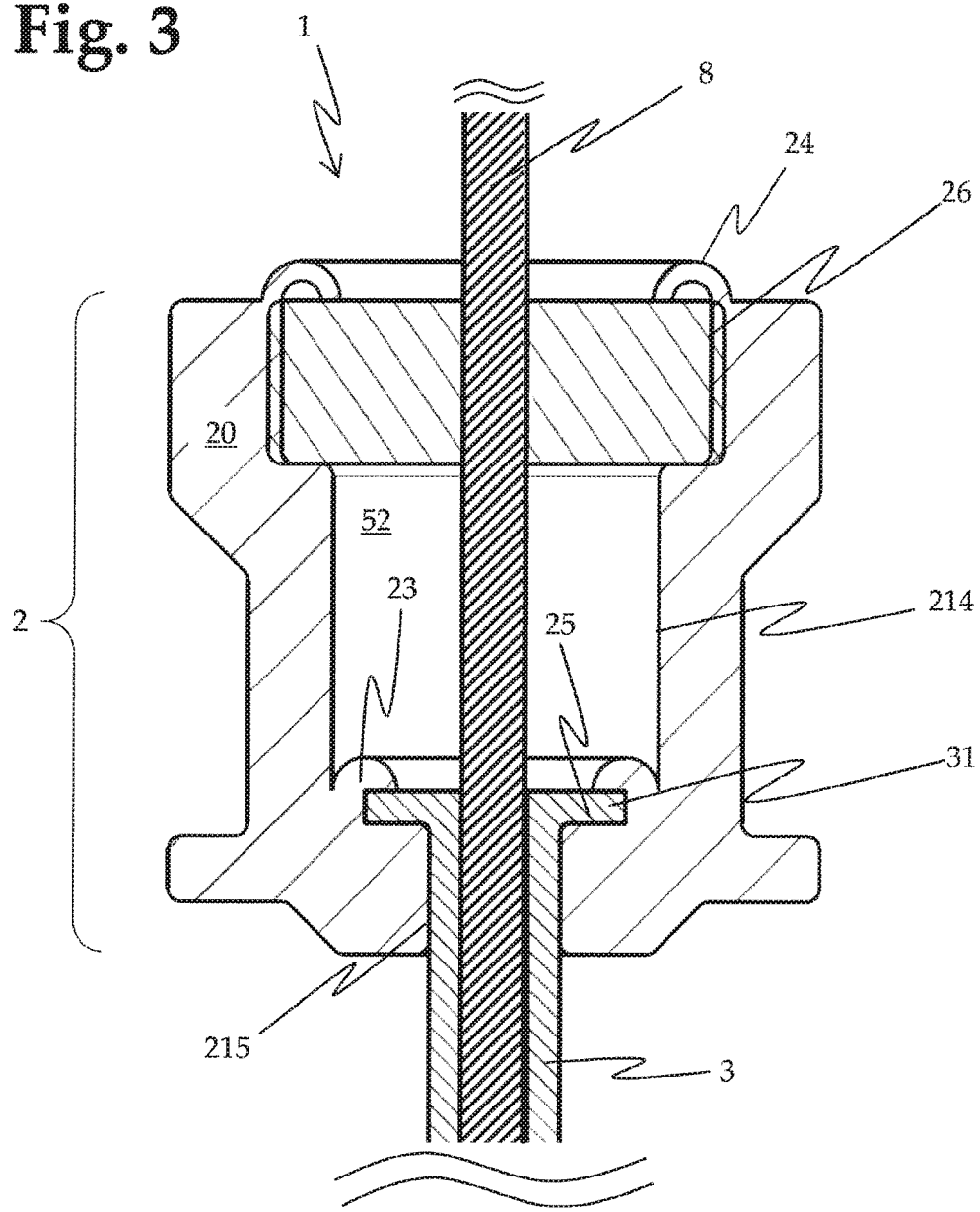
FIG. 3 schematically shows the cannula unit of FIG. 2, with the piercing needle in place.

A second embodiment of a cannula unit 1 according to this disclosure is disclosed in a cross-sectional view in FIGS. 2 and 3, without and with mounted piercing needle 8. The assembled cannula unit 1 comprises a cannula 3, of which the distal end is visible, and a housing 2, to which the cannula 3 is mounted. The body of the housing is realized as one monolithic element 20. The outer shape of housing body 2 is chosen such that the housing body, and thus the cannula unit 1, can be mounted, e.g., to an infusion site interface. A septum 4 is arranged in a seat 26 of the body 2, and is held in place by a crimp connection 24 similar to the cannula unit of FIG. 1. The explanations made further above in regard to suitable materials for body 2 and cannula 3 apply also for this as well as all following embodiments of cannula units according to this disclosure.

The septum 4 sealingly closes an upper, distal end of an upper bore 214 of housing body 2, thereby defining a fluid chamber 52 between septum 4 and the distal end of cannula 3, its fluid channel 51 opening toward the fluid chamber 52. As can be seen in FIG. 3, the piercing needle 8 penetrates septum 4, and is arranged inside the fluid channel of cannula 3 in such a way that the wall of cannula 3 abuts the needle surface, but only with a minimum amount of friction, in order to ensure both an insertion of the cannula/needle structure without wrinkling up of the cannula, and the withdrawal of the piercing needle 8 after insertion into the body tissue.

The cannula unit 1 as shown in FIG. 2 differs from the first embodiment particularly in the way the cannula 3 is clamped to the body 2. The cannula 3 is arranged in a lower bore 215 of the body, having essentially the same diameter as the cannula. At its distal end, cannula 3 is provided with a flange 31 arranged in a corresponding seat 25 of the body. The flange 31 is held in place in the seat 25 by a crimping connection 23. In order to achieve a fluid-tight connection between inner volume 52 and fluid channel 51 of cannula 3, the crimp connection is prepared in such a way that the outer rim of the flange 31 is compressed by the rim of the crimp 23.

The second embodiment of a cannula unit according to this disclosure as discussed above has the advantage that it comprises one less separate compound, which further simplifies the assembly process and further reduces potential sources of malfunctions.

For manufacturing a cannula unit according to the second embodiment, in a first step a flexible cannula 3 is provided with a horizontal flange 31, for example by deforming an end of the cannula with an appropriate tool. The cannula is then threaded into the through-hole of body 2, until the flange 31 is located in the circular seat 25 of the body. A suitable crimp structure around the seat 25 is then thermally deformed, in order to make the crimp connection 23. The parameters of this step must be chosen such that after the crimping step is finished, the rim of the crimp structure presses the flange 31 against the body 2, in order to achieve a sealing connection. Now the septum 4 is mounted, similar to the method discussed above in the context of the first embodiment, arriving at the state in FIG. 2. The cannula unit as such is completed.

As a next step, the piercing needle is inserted, by penetrating the septum 4 and threading the needle through cannula 3, until a tipped end of piercing needle 8 protrudes from the proximal opening of cannula 3. Alternatively, and similar to the first embodiment, the piercing needle may already be inserted into the cannula unit directly after the forming of flange 31, or after the completed mounting of the cannula in body 2.

As explained further above for the first embodiment, the body 2 and/or the piercing needle 8 can now be connected with other functional structures.

Figure 4:
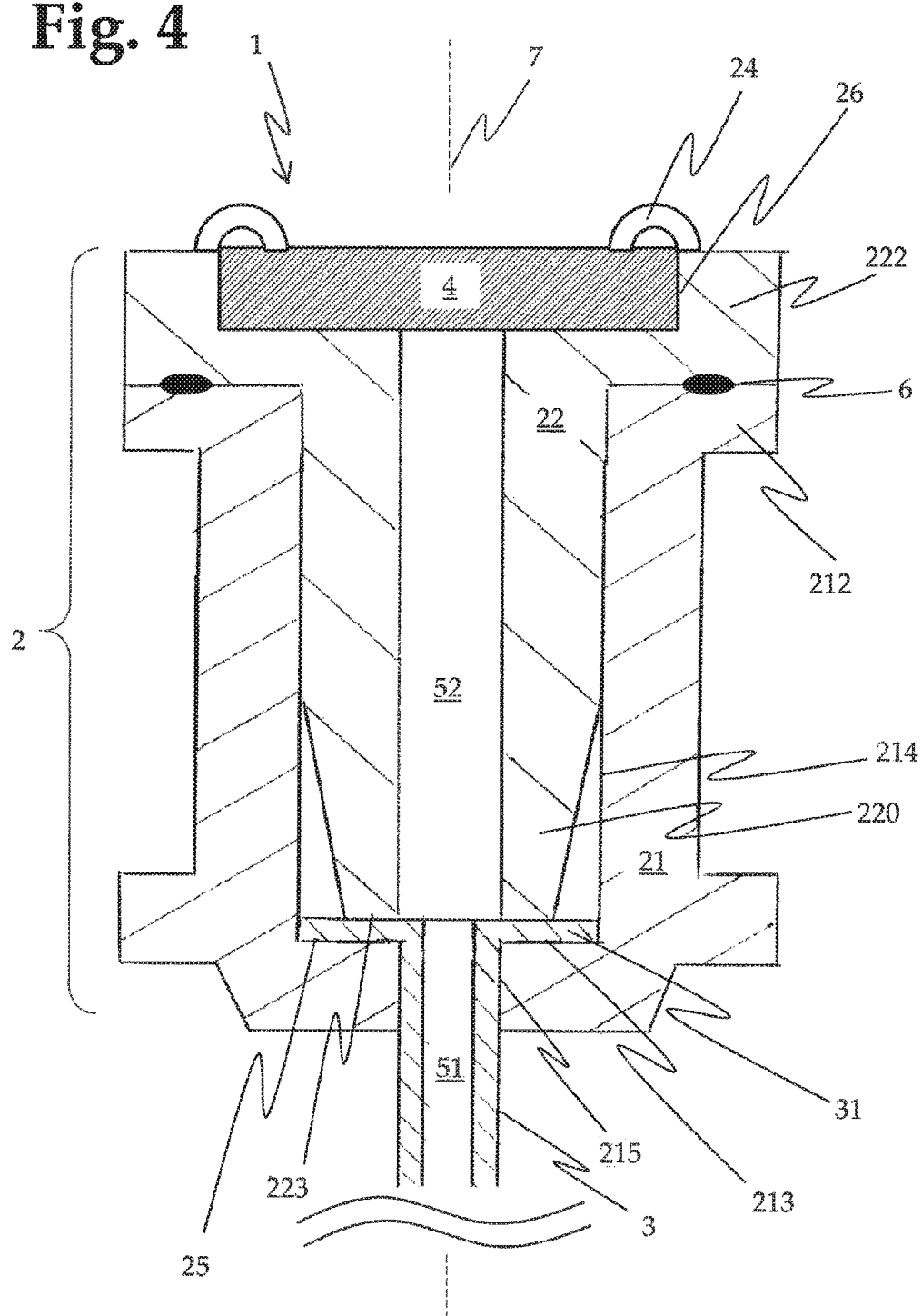
FIG. 4 schematically shows a cross section of a third embodiment of a cannula unit according to this disclosure.

A third embodiment of a cannula unit 1 according to this disclosure is shown in FIG. 4. The body of housing 2 comprises a first part 21 and a second part 22. The first part 21 comprises a through-hole consisting of two cylindrical bores 214, 215 with different diameters, and an outer circumferential flange 212. A cannula 3 having a flange 31 at its distal end is mounted to body 2. The cannula 3 protrudes through a lower bore 215 of first part 21, and the flange 31 abuts the bottom 213 of an upper bore of the first part 21. The second part 22 comprises a bushing 220 with a through-hole, and an outer circumferential flange 222. The bushing 220 is arranged in the upper bore 214 of first part 21, and the flange 222 of second part 22 abuts the flange 212 of first part 21. In the assembled cannula unit 1, the two parts 21, 22 are permanently connected to each other, in the given exemplary embodiment by ultrasonic welding points 6 between the two flanges 212, 222. A septum 4 is arranged in seat 26 of second part 22, and held in place by crimp connection 24, as discussed above for the previous embodiments. The septum 4 sealingly closes an upper end of an inner bore of second part 22, thereby defining a fluid chamber 52 that is fluidly connected with fluid channel 51 of cannula 3. The dimensions of the two parts 21, 22 and the flange 31 of cannula 3 are chosen such that a proximal edge 223 of bushing 220 presses the cannula flange 31 against bottom 213, thereby compressing flange 31 and sealingly connecting the inner bore of second part 22 and cannula 3.

The manufacturing method for this third embodiment of a cannula unit according to this disclosure is similar to the methods discussed further above. After providing a cannula 3 with a flange 31 on its end, and placing the cannula into first part 21, the bushing 220 is inserted into the upper bore 214 of first part 21, until the two flanges 212, 22 abut each other. The bushing 220 is aligned to longitudinal axis 7 by cylindrical upper bore 214. After permanently connecting the two flanges 212, 222 by ultrasonic welding 6, septum 4 is put in place, and the crimp connection 24 is completed. As for the other discussed method variants, the piercing needle 8 may be inserted into cannula 3 directly after the formation of cannula flange 31, after the fixation of cannula 3 and the permanent connection of the two parts of the housing body 2, or after the mounting of the septum 4 to the housing body 2.

The embodiments of cannula units as discussed so far have been equipped with only one septum, which can be used both for withdrawing the piercing means, and for establishing a fluid connection with an infusion pump. However, cannula units according to this disclosure can also be equipped with a separate connection element for connecting the cannula unit to an upstream infusion pump. For example can the cannula unit be provided with a further connector port with septum, fluidly connected to the fluid chamber by a fluid channel in the housing body. Examples of such cannula units are disclosed, e.g., in FIG. 1B of U.S. Publication No. 2012/0296290 A1, and in FIG. 21 of U.S. Publication No. 2008/0228144 A1, the disclosures of which are hereby incorporated herein by reference in their entirety. The cannula units according to this disclosure as discussed so far can be adapted by a skilled person to such complex cannula unit structures. The same applies for the manufacturing methods for such cannula units.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

LIST OF REFERENCE NUMERALS 1 cannula unit
2 housing body, housing
20 single part of body
21 first part of body
211 receptacle, conical bore
212 flange
213 bottom of upper bore of first part
214 upper bore
215 lower bore
22 second part of body
220 bushing
221 conical bushing
222 flange
223 proximal edge of bushing
23 crimp connection for fixation of tube
24 crimp connection for fixation of septum
25 seat for cannula flange
26 seat for septum
3 cannula
31 flange
32 funnel-shaped end of cannula
4 septum
51 fluid channel
52 fluid chamber
6 ultrasonic welding point
7 longitudinal axis
8 piercing needle

What is claimed is:

1. A method for manufacturing a cannula unit, comprising:
as a first step, providing a flexible cannula with a flexible end area with an opening with increased diameter, the flexible end area having a funnel-shaped wall that has an inner surface and an outer surface that are substantially parallel;
providing a housing having a first housing part and a second housing part;
connecting the flexible end area of the flexible cannula to the housing;
wherein the funnel-shaped wall of the flexible end area of the flexible cannula is positively locked to the housing by clamping, wherein the funnel-shaped wall fully retains a funnel shape when clamped;
further wherein the second housing part has an outside surface facing an inside surface of the first housing part and the cannula is sandwiched between the inside surface and the outside surface at a location where the outside surface has an inclination greater than an inclination of the inside surface; and
permanently attaching the first housing part to the second housing part after clamping the flexible end area of the flexible cannula to the housing.

2. The method according to claim 1, wherein the flexible end area of the flexible cannula is connected to the housing by crimping.

3. The method according to claim 1, wherein the flexible end area of the flexible cannula is connected to the housing by clamping the flexible end area of the flexible cannula between the first housing part and the second housing part.

4. The method according to claim 3, wherein the first housing part and the second housing part are provided as two separate parts.

5. The method according to claim 4, wherein the first housing part and the second housing part have complementary funnel shapes.

6. The method according to claim 1, wherein the permanently attaching of the first housing part to the second housing part is made by ultrasonic welding and/or adhesive bonding.

7. The method according to claim 1, wherein a piercing element is mounted to the flexible cannula by threading the piercing element on or in the flexible cannula.

8. The method according to claim 1, further comprising mounting a septum to the housing.

9. The method according to claim 8, wherein the mounting is done by crimping.

10. The method according to claim 1, wherein the funnel-shaped wall of the flexible cannula is connected to the housing by crimping.

11. The method according to claim 1, wherein the first housing part and the second housing part have complementary funnel-shaped portions and the funnel-shaped wall of the flexible cannula is clamped between the complementary funnel-shaped portions.

12. The method according to claim 11, wherein the funnel-shaped wall of the flexible cannula is crimped between the complementary funnel-shaped portions of the first housing part and the second housing part.

13. The method according to claim 12, wherein the complementary funnel-shaped portions of the first housing part and the second housing part form a tapering gap within which the funnel-shaped wall of the flexible cannula is disposed.

14. A cannula unit, comprising:
a housing having a first housing part and a second housing part, wherein the second housing part has an outside surface facing an inside surface of the first housing part; and
a flexible cannula having a flexible end area comprising a funnel-shaped wall before the flexible cannula is connected to the housing, wherein the funnel-shaped wall has an inner surface and an outer surface that are substantially parallel;
wherein the funnel-shaped wall of the flexible end area of the flexible cannula is positively locked to the housing by clamping, and the funnel-shaped wall fully retains a funnel shape when clamped;
wherein, an outer side of the funnel-shaped wall contacts the first housing part, an inner side of the funnel shaped wall contacts the second housing part, and a septum is attached to the second housing part;

wherein the cannula is sandwiched between the inside surface and the outside surface at a location where the outside surface has an inclination greater than an inclination of the inside surface;

wherein a distal end of the second housing part terminates within the funnel-shaped wall of the cannula.

15. The cannula unit according to claim 14, wherein said flexible end area of the flexible cannula includes a flange.

16. The cannula unit according to claim 14, wherein the flexible end area of the flexible cannula is crimped to the housing.

17. The cannula unit according to claim 14, wherein the flexible end area is clamped between the first housing part and the second housing part.

18. The cannula unit according to claim 17, wherein the first housing part and the second housing part are separate parts.

19. The cannula unit according to claim 18, wherein the first housing part and the second housing part have complementary funnel shapes.

20. The cannula unit according to claim 18, wherein the first housing part and the second housing part are permanently connected to each other.

21. The cannula unit according to claim 20, wherein the permanent connection comprises ultrasonic welding and/or adhesive bonding.

22. The cannula unit according to claim 14, further comprising a piercing element threaded on or in the flexible cannula.

23. The cannula unit according to claim 14, wherein the septum is mounted to the second housing part by crimping.

24. A method for manufacturing a cannula unit, comprising:

providing a housing having a first housing part and a second housing part;

providing a flexible cannula with an end area having a flange that extends substantially perpendicularly to a longitudinal axis of the housing;

connecting the end area of the flexible cannula to the housing, wherein the end area of the flexible cannula is positively locked to the housing by clamping, and wherein the flexible cannula is provided with the flange on the end area before positively locking the end area to the housing;

crimping the end area of the flexible cannula between the first housing part and the second housing part; and after clamping the end area of the flexible cannula to the housing, permanently connecting the first housing part and the second housing part.

25. The method according to claim 24, wherein the first housing part and the second housing part and the end area of the flexible cannula have corresponding funnel shapes.

26. The method according to claim 24, wherein permanently connecting the first housing part and second housing part of the housing comprises ultrasonic welding and/or adhesive bonding.

* * * * *